United States Patent [19]

Regenass et al.

[11] 4,456,389
[45] Jun. 26, 1984

[54] HEAT FLOW CALORIMETER

[75] Inventors: Willy Regenass; Gerhard Giger, both of Muttenz; Kaspar Kuster, Allschwil; Heinz Achermann, Uster, all of Switzerland

[73] Assignee: Ciba-Geigy Corporation, Ardsley, N.Y.

[21] Appl. No.: 270,185

[22] Filed: Jun. 3, 1981

[30] Foreign Application Priority Data

Jun. 10, 1980 [CH] Switzerland ............... 4465/80

[51] Int. Cl.$^3$ ............................................. G01K 17/00
[52] U.S. Cl. ................................................. 374/31
[58] Field of Search ................... 374/31, 33, 34, 36; 165/34, 39, 40

[56] References Cited

U.S. PATENT DOCUMENTS

| | | | |
|---|---|---|---|
| 1,247,998 | 11/1917 | Parr | 374/34 |
| 2,986,028 | 5/1961 | Shawhan | 374/33 |
| 3,593,577 | 7/1971 | Monner | 374/34 |
| 3,994,164 | 11/1976 | Regenass et al. | 374/31 |

FOREIGN PATENT DOCUMENTS 2004647A 5/1979 United Kingdom .

*Primary Examiner*—Herbert Goldstein
*Attorney, Agent, or Firm*—Harry Falber

[57] ABSTRACT

The heat exchange mantle of a reaction vessel is connected with a circulating pump and a chamber provided with an electrical heating coil to form a heat exchange circulation system. To this main circulation system, a cooling circulation system comprising a circulating pump and a heat exchanger is connected by way of a continuously operable valve. The temperature of the medium circulating in the main circulation system can be very effectively and rapidly influenced by dosed addition of cooled circulation medium from the cooling circulation system into the main circulation system as well as by heating with the electrical heating coil. In the cooling circulation system, in the reaction vessel and in its mantle, temperature sensors are arranged which are linked to a control computer. The computer controls the electrical heating coil and the valve in such a manner that the temperature in the reaction vessel or in its mantle, respectively, has a desired distribution prescribed by the operational mode. Furthermore, the computer controls a recorder which records the heat flow from the reaction vessel.

10 Claims, 7 Drawing Figures

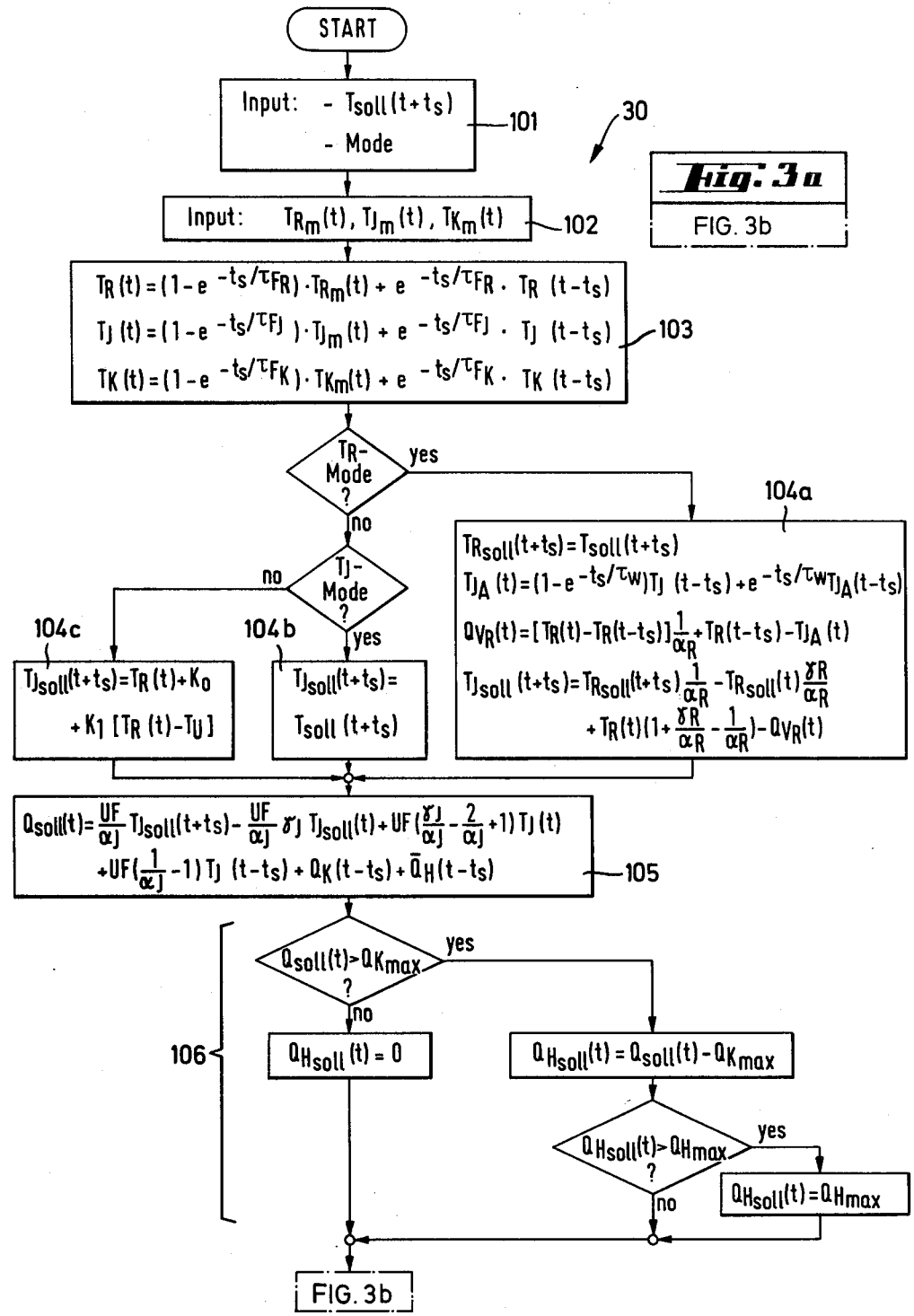

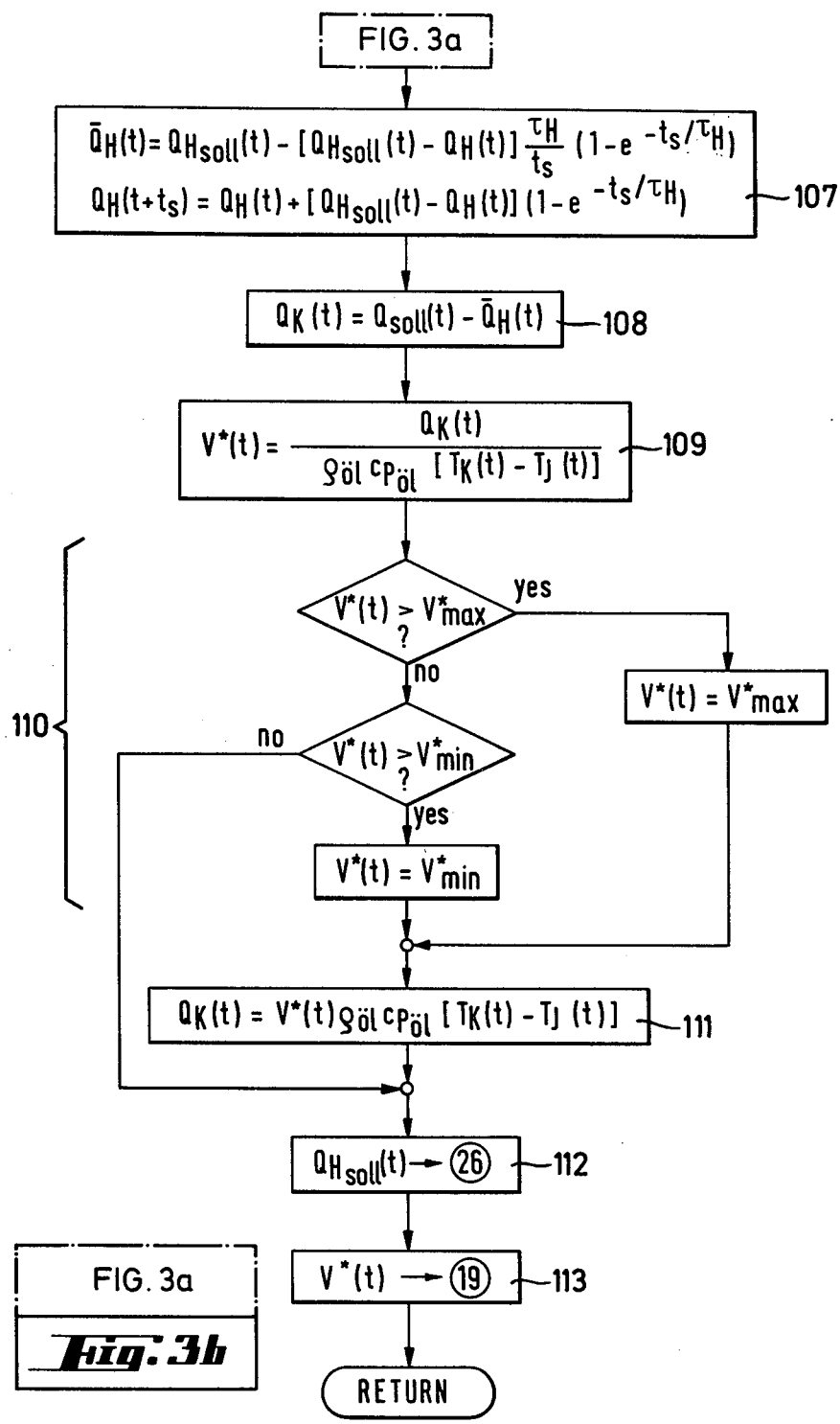

HEAT FLOW CALORIMETER

BACKGROUND OF THE INVENTION

The invention relates to a heat flow calorimeter having a reaction vessel provided with a heat exchange mantle, a circulation system comprising the mantle of the reaction vessel for a heat transfer medium, means for circulating the medium in the circulation system, a source of cooled circulation medium connectable to the circulation system, means for heating the heat transfer medium in the circulation system and temperature sensors in the reaction vessel, in its mantle and in the source, and an electronic control system driven by these temperature sensors which controls the temperature of the circulation medium through cooling due to supply of cooled circulation medium from the source or, respectively, through heating by means of the heating means in accordance with a given desired temperature pattern in the reactor and/or in its mantle, and with means which record changes, with time, of temperature $(T_R)$ in reactor and $(T_J)$ mantle and/or the difference of $(T_R - T_J)$ of these temperatures, as well as a method for the operation of the same, wherein the temperature of the heat transfer medium in a main circulation system is controlled by heating or by supply of cooled medium from the cooling circulation system, respectively.

One of the most efficient and universal heat flow calorimeters of the type under discussion is described, e.g., in U.S. Pat. No. 3,994,164. In this calorimeter, the control of the circulation temperature and therewith of the temperature in the reaction vessel is effected by controlled displacement of circulation medium, depending on which is required, by a hotter or colder circulation medium from a corresponding reservoir tank. For this purpose, both tanks are connected in parallel, each by way of a section, containing a valve or a throttle, of the medium circulation system wherein the valves are operated by an electronic control which cooperates with various temperature sensors in the reaction vessel and in its mantle. The tank temperatures are adjusted via separate regulators of the circulation temperature with a fixed delay, i.e. the temperature of the medium in the tanks is always higher or lower, by a determined constant amount, than the temperature of the heat transfer medium circulating through the mantle of the reaction vessel.

The control of the circulation medium temperature used in this calorimeter has shown itself to be extremely effective but it is costly from a viewpoint of construction and control techniques. Thus, for instance, two tanks with corresponding inlets and valves are necessary, and the temperatures of the contents of two tanks must be constantly adjusted with highest precision. Furthermore, especially because of the two tanks, the known heat flow calorimeter is still relatively bulky.

OBJECTS AND SUMMARY OF THE INVENTION

In the present invention, these drawbacks are to be avoided and a heat calorimeter is to be provided which is as simple as possible as far as its construction and control techniques are concerned, and which is furthermore as structurally compact as possible. A further task of the invention consists in providing an especially appropriate method for the operation of the apparatus.

These tasks underlying the invention are accomplished, in accordance with the invention, by a heat flow calorimeter of the initially described type wherein the source of the cooled circulation medium is a separate cooling circulation system which comprises a circulating pump, a cold-generating source (referred to hereinafter as "cold source" for short) and ducts required for these two elements to form a circulation system which is linked via a valve to the initially mentioned circulation system for the reaction vessel which latter system is designated in the following as the main circulation system; these tasks are further accomplished by the initially described operating method wherein there is never fed to the main circulation system a smaller amount of cooled circulation medium than corresponds to a determined minimum cooling performance; while, when the required amount of heat $(Q_{soll})$ of the circulation medium detected by the control is larger than this minimum cooling performance, there is fed the required amount of heat via the heating means to the main circulation system.

Preferably, the valve connects the pressure side of the circulation pump of the cooling circulation system with the suction side of the circulating means of the main circulation system leaving as little dead volume as possible. The cooling circulation system can additionally be connected on the suction side of its circulating pump by a compensating line with the main circulation system. The cold source can also be a heat exchanger with connections for passage of a cooling medium. At the entry side and/or outlet side of the valve, a flushing circulation system can be provided. Preferably, the valve is connected with a bypass loop of the cooling circulation system. The valve can be connected practically directly to the inlet of the circulating means of the main circulation system. The heating means can also comprise an electrical heating coil.

The heating means preferably comprise a substantially cylindrically shaped chamber inserted in the main circulation system and having a cross-section substantially larger than that of the circulation ducts, a substantially cylindrical displacement body coaxially arranged in the chamber, and an electrical heating coil arranged in the hollow space between the displacement body and the inner wall. The displacement body can be driven by a motor and rotate about its axis. The circulating means of the main circulation system and the circulating pump of the cooling circulation system can also be driven by a common driving motor via a common drive shaft. Preferably, the displacement body is driven by the same motor and via the same drive shaft as the circulating means.

BRIEF DESCRIPTION OF THE DRAWING

In the following, the invention is explained in more detail with reference to the drawing, wherein.

DETAILED DESCRIPTION OF THE EMBODIMENTS SHOWN IN THE DRAWING

Figure 1:
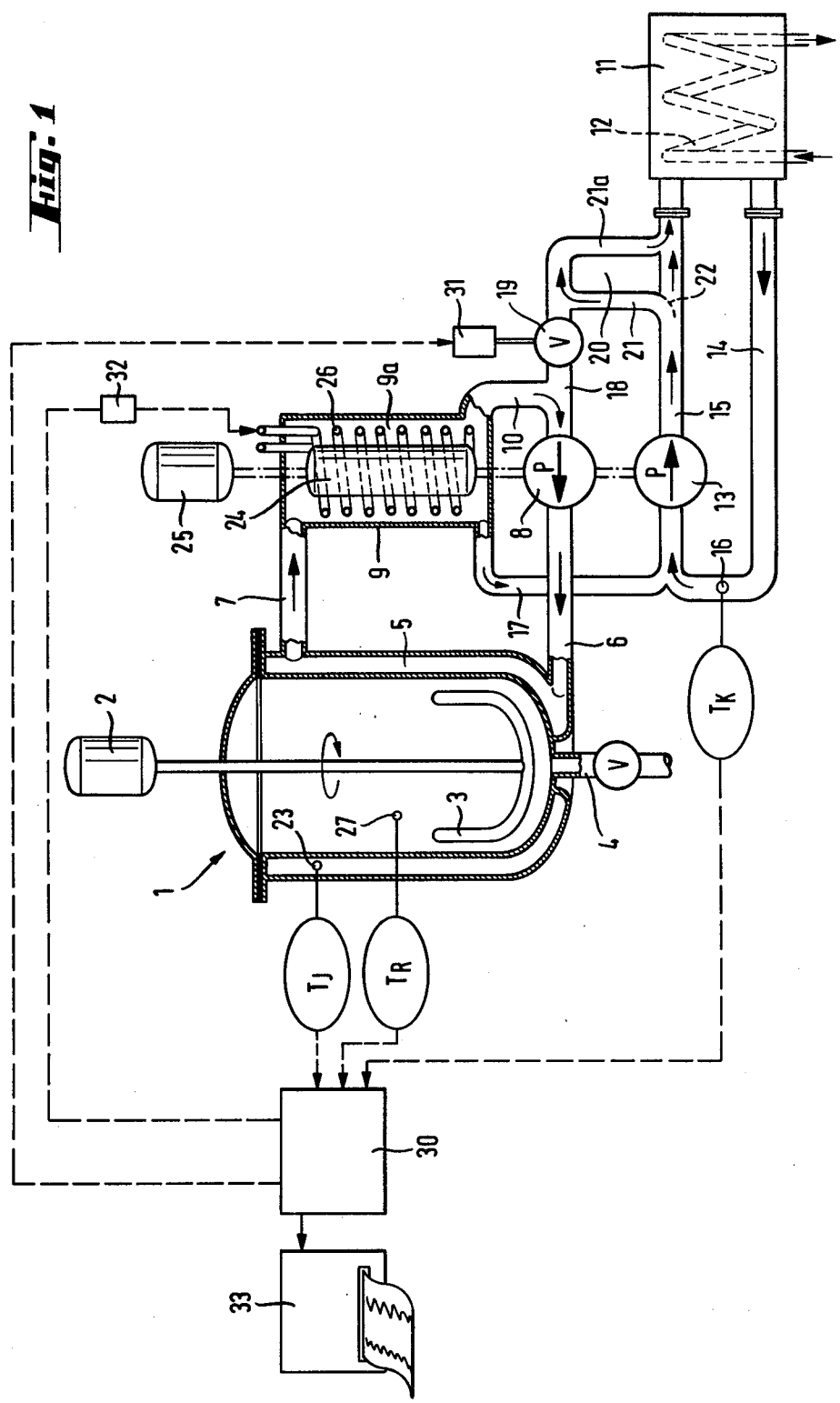
FIG. 1 shows a schematic representation of an embodiment of a heat flow calorimeter according to the invention.

The central part of the heat flow calorimeter shown only schematically in FIG. 1 is a double-walled reaction vessel with a stirrer 3 driven by a motor 2 and an outlet 4. To the heating/cooling mantle 5 of the reactor 1 there are associated two ducts 6 and 7 which are connected with the pressure side of a circulating pump 8 or the inlet of a heating chamber 9. From the outlet side of the heating chamber 9 a duct 10 leads on to the suction side of the circulating pump 8. The mantle 5, the duct 7, the heating chamber 9, the duct 10, the circulating pump 8 and the duct 6, constitute together a closed circulation system, designated as the main circulation system hereinbefore; therein circulates a liquid heat transfer medium, for example oil, by means of which the temperature in the reaction vessel is controlled.

Beside the main circulation system, a second circulation system also is provided, which is referred to as the cooling circulation system hereinafter. The latter consists of a cooler 11 with a heat exchange coil 12 and a circulating pump 13 as well as two lines 14 and 15 forming together with the cooler 11 and the pump 13 a closed circulation system. In the cooling circulation system the same heat transfer medium circulates as in the main circulation system. The heat exchanger coil 12 is connected to any cold source (not shown) of appropriate capacity. For measuring the temperature $T_K$ of the medium in the cooling circulation system, a temperature sensor 16 is disposed in the line 14.

The main circulation system and the cooling circulation system are connected with one another through two further lines 17 and 18. Line 17 leads from the outlet side of the heating chamber 9 to the suction side of the circulating pump 13. The line 18, in which a continuously operable valve 19 is mounted, leads directly from the suction side of the main circulating pump 8 to a transfer loop 20 having two branches 21 and 21a which loop is connected with the line 15 at two spaced apart locations and bypasses the line portion lying therebetween. A deviation element 22 in the line 15 directs a part of the flowing medium into loop 20 so that the latter is constantly traversed by medium, as are all other parts. The connecting line 18 between the cooling circulation system is a very short one. In practice, the valve 19 is directly connected, at the pump inlet, with the duct 10 and directly with the loop 20 so that this connecting line only consists of the valve 19 itself. By this arrangement it is achieved that no noteworthy dead volumes exist between the cooling and the main circulation system; in such dead volumes, the cooling medium could assume a temperature different from that in the cooling circulation system, thereby impairing the accuracy of control.

By opening valve 19 a controlled amount of cooler medium can be transferred from the cooling circulation system into the main circulation system and thus its temperature $T_J$ which is determined by a sensor 23 in reactor mantle 5 can be influenced. The volume of medium which is thereby displaced in the main circulation system, flows off through the line 17 into the cooling circulation system.

The heating chamber 9 contains an essentially cylindrical displacement body 24 which is arranged coaxially in the chamber and is rotatingly driven by a motor 25. On the same drive shaft as body 24, the rotors of both circulating pumps 8 and 13 are also mounted, whereby an especially compact construction of the whole apparatus is achieved.

In the annular hollow space 9a between the displacement body 24 and the wall of the heating chamber 9, an electrical heating coil 26 is arranged. Because of this embodiment of the heating chamber it is possible to provide with smallest circulation volume a relatively efficient and corresponding large electrical heating coil. The rotation of the displacement body furthermore effects a good mixing of the medium flowing through the heating chamber and thus an improved heat transfer.

The temperatures $T_K$ of the medium in the cooling circulation system and $T_J$ of the medium in the main circulation system in reactor mantle 5 detected by sensors 16 and 23, as well as the temperature $T_R$ of the reactive mixture in reactor 1, detected by a further sensor 27, constitute the input values for an electronic regulator 30 controlling the calorimeter. The regulator is preferably a digital computer which can also, at the same time, take over the evaluation of heat flow measurements, beside its actual regulative functions. Basically, any highly efficient micro- or minicomputer system can be used as the regulator, for example the LSI-11/2 system of Digital Equipment Corporation.

Regulator 30 controls valve 19 and the heating coil 26 via appropriate interfaces 31 and 32 as well as a recorder 33 serving as output device.

Figure 2:
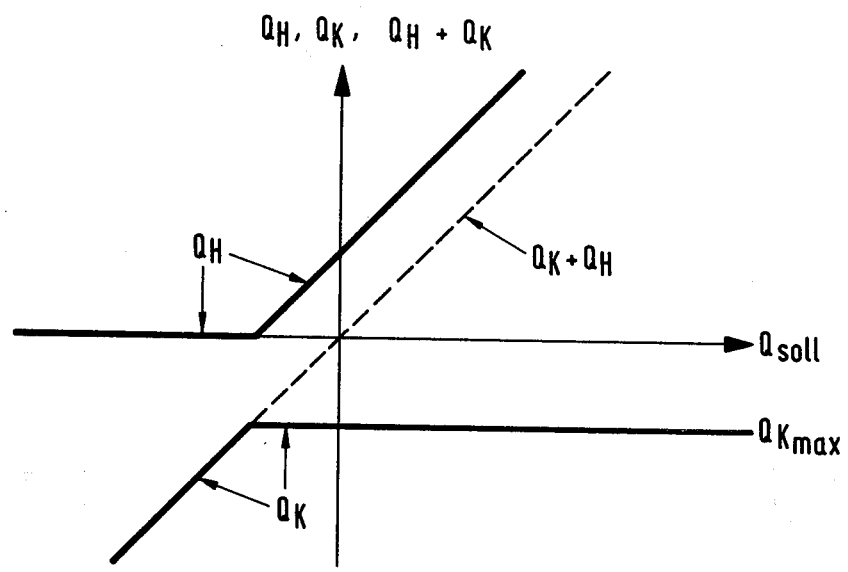
FIG. 2 shows a regulator characteristic curve, FIG. 3 a flow chart of the regulating method, FIGS. 4 to 6 a schematic representation each of three variations of the calorimeter of FIG. 1 and FIG. 7 a view of the construction of the calorimeter of FIG. 1.

The general functioning of the heat exchange circulation system of the heat flow calorimeter according to the invention can be seen in the desired heating-cooling performance characteristic curve shown in FIG. 2. The abscissa shows the heating/cooling performance $Q_{soll}$ to be provided at each instant in order to reach or maintain a determined temperature $T_J$ in the reactor mantle, and the ordinate shows the contributions $Q_H$ and $Q_K$, respectively, to be made to this end by the heating system 26 and the cooling circulation system; the sum of $Q_H + Q_K$ must, of course be equal to the desired heat performance $Q_{soll}$.

As shown by the characteristic curve, the regulation is so designed that constantly at least a certain minimal amount $Q_{K\,max}$ of heat, e.g. 200 watt, is transmitted and the possible difference from the demanded value of $Q_{soll}$ is compensated by corresponding supply of heat $Q_H$ (the designation of $Q_{K\,max}$ for the said minimal cooling performance is due to the fact that a cooling performance corresponds to a negative heating performance). Sudden changes of the required heat performance $Q_{soll}$ are compensated by corresponding adjustment of the cooling performance $Q_K$ wherein, of course, temporary deviations from the characteristic curve shown in FIG. 2 will occur. By corresponding adjustment of the heating performance $Q_H$ it is then attempted to return to the shown characteristic curve as quickly as possible. This regulative philosophy according to the invention makes use of the circumstance that in the described heat flow calorimeter rapid temperature changes can be regulated by means of a cooling system which responds very quickly.

The heat flow calorimeter according to the invention can basically be operated according to three different modes. These are the socalled $T_R$-mode wherein the desired temperature $T_R$ in the reactor is the determining command variable, the $T_J$-mode in which the temperature $T_J$ in the reactor mantle is the decisive command variable and an adiabatic mode wherein the command variable results from the reactor temperature and the heat transmission to the surroundings.

In FIG. 3 the flow chart of the electronic regulating method carried out by computer 30 is depicted. The flow chart describes a regulating cycle which is repeated in regular time intervals $t_s$ of, e.g., 2 seconds. For the flow chart the following definitions hold:

| | |
|---|---|
| $c_{poil}$ | specific heat of the heat transfer liquid |
| $c_{pR}$ | specific heat of the reactor liquid |
| F | effective exchange area |
| $K_o$ | constant for calculation of the emission in adiabatic mode |
| $K_1$ | constant for calculation of the emission in adiabatic mode |
| $Q_H$ | instant heat performance of the throughflow heating system |
| $\overline{Q}_H$ | median heat performance of the throughflow heating system during a scanning period |
| $Q_{Hmax}$ | maximal heat performance of the throughflow heating system |
| $Q_{Hsoll}$ | desired heating performance of the throughflow heating system |
| $Q_K$ | cooling performance by inflow of cold heat transfer liquid from a cooling circulation system into the main circulation system |
| $Q_{Kmax}$ | cooling performance (lowest permissable value) |
| $Q_{soll}$ | desired sum of cooling and heating performance |
| $Q_{VR}$ | estimated power loss in the reactor |
| $t_s$ | scanning time increment |
| $T_J$ | filtered value of mantle temperature |
| $T_{Jm}$ | measured value of mantle temperature |
| $T_{Jsoll}$ | required value of mantle temperature |
| $T_{JA}$ | mantle temperature delayed by the wall capacity of the reactor |
| $T_K$ | filtered value of cooling cycle temperature |
| $T_{Km}$ | measured value of cooling cycle temperature |
| $T_R$ | filtered value of the reactor temperature |
| $T_{Rm}$ | measured value of the reactor temperature |
| $T_{Rsoll}$ | required value of the reactor temperature |
| $T_{soll}$ | input value of required temperature |
| $T_U$ | ambient temperature |
| U | total heat transfer coefficient |
| $V_J$ | volume of main circulation system |
| $V_R$ | volume of reactor |
| $V^*$ | volume flow of heat transfer liquid from from the cooling circulation system to the main circulation system |
| $V^*_{max}$ | maximal volume flow |
| $V^*_{min}$ | minimal volume flow |
| $\alpha_J = 1 - e^{-t_s/\tau_J}$ | |
| $\alpha_R = 1 - e^{-t_s/\tau_R}$ | |
| $\beta_J$ | desired ratio of required value deviations of the mantle temperature for two successive scan times |
| $\beta_R$ | desired ratio of required value deviations of the reactor temperature for two successive scan times |
| $\gamma_J = \beta_J e^{-t_s/\tau_J}$ | |
| $\gamma_R = \beta_R e^{-t_s/\tau_R}$ | |
| $\rho_{oil}$ | density of heat transfer liquid |
| $\rho_R$ | density of reactor liquid |
| $\tau_{FJ}$ | time constant of filter for mantle temperature |
| $\tau_{FK}$ | time constant of filter for cooling circulation system temperature |
| $\tau_{FR}$ | time constant of filter for reactor temperature |
| $\tau_H$ | time constant of throughflow heating system |

$$\tau_J = \frac{\rho_{oil} \cdot c_{poil} \cdot V_J}{U \cdot F}$$

$$\tau_R = \frac{\rho_R \cdot c_{pR} \cdot V_R}{U \cdot F}$$

$\tau_W = \tau_{FR} - \tau_{wall}$
$\tau_{wall}$ = time delay of mantle temperature caused by wall capacity of reactor.

As first step 101 of the regulating cycle, the input of the regulation mode and the desired required value $T_{soll}$ of reactor or mantle temperature, respectively, is carried out. This required value can, for instance, be constant for all cycles (isothermal operation mode) or have any predetermined time distribution (temperature-programmed mode of operation).

In the next step 102, the temperature $T_{Rm}(t)$, $T_{Jm}(t)$ and $T_{Km}(t)$ reigning at the time t in the reactor, in its mantle and in the cooling circulation system, are measured and, in step 103, these measured values are then filtered, affording the filtered temperature values $T_R(t)$, $T_J(t)$ and $T_K(t)$ used in the following.

Now, an interrogation of the chosen regulating mode takes place whereupon, for each of the three possible cases according to one of steps 104a–104c, the required value $T_{Jsoll}(t+t_s)$ of the mantle temperature to be reached until the next cycle is calculated, which then constitutes the value governing all further steps. The meaning of steps 104 and 104c is self-evident. Step 104a calculates the mantle temperature required for achieving the desired reactor temperature, taking into consideration various system parameters. The theoretical background therefor is described e.g. in J. Ind. & Chem. Eng. Vol. 24, No. 2, March 1978, pages 360–364.

In the next step 105, the total heating/cooling performance $Q_{soll}(t)$ necessary for reaching the calculated required value $T_{Jsoll}(t+t_s)$ is calculated (positive values mean overall heat supply, negative values heat loss).

The following step 106 copies the regulation characteristic curve according to FIG. 2: when the required heat performance $Q_{soll}(t)$ is not larger than the minimal cooling performance $Q_{Kmax}$ (i.e., when a stronger cooling than $Q_{Kmax}$ is necessary) the required heat supply $Q_{Hsoll}(t)$ is set equal to zero (no heating via heating via heating coil 26). However, if $Q_{soll}(t)$ is larger, then the required heat performance $Q_{Hsoll}(t)$ is set equal to the difference of required total heat performance $Q_{soll}$ and the minimal cooling performance $Q_{Kmax}$. In case this differential value surpasses the maximal heat performance $Q_{Hmax}$ of the heating coil 26, which condition depends on the dimensioning of the system, $Q_{Hsoll}(t)$ is set to equal this maximal heating performance.

In step 107 the calculation of the median heating performance $\overline{Q}_H(t)$ during the next period (time interval $t_s$) as well as the instant heating performance $Q_H(t+t_s)$ at the end of this period are carried out.

In the next step 108 the then actually required cooling performance $Q_K(t)$ is determined; and, in the following step 109, the volume influx $V^*(t)$ of the heat exchange medium necessary therefor, from the cooling circulation system to the main circulation system.

Steps 110 and 111 take into account the characteristic curve of valve 19. If the required volume influx $V^*(t)$ surpasses the maximal throughflow of the valve or falls below the minimal throughflow, the influx is set equal to the corresponding limit value and, in step 111, the actual cooling performance is then calculated for use in the next regulating cycle.

In the last two steps 112 and 113 of the regulating cycle, the control of the heating coil 26 and valve 19 is carried out according to values $Q_{Hsoll}(t)$ or $V^*(t)$, respectively, via the interfaces 31 and 32 which are presumed to be known. Thereupon, the cycle is repeated starting with step 101.

Figure 4:
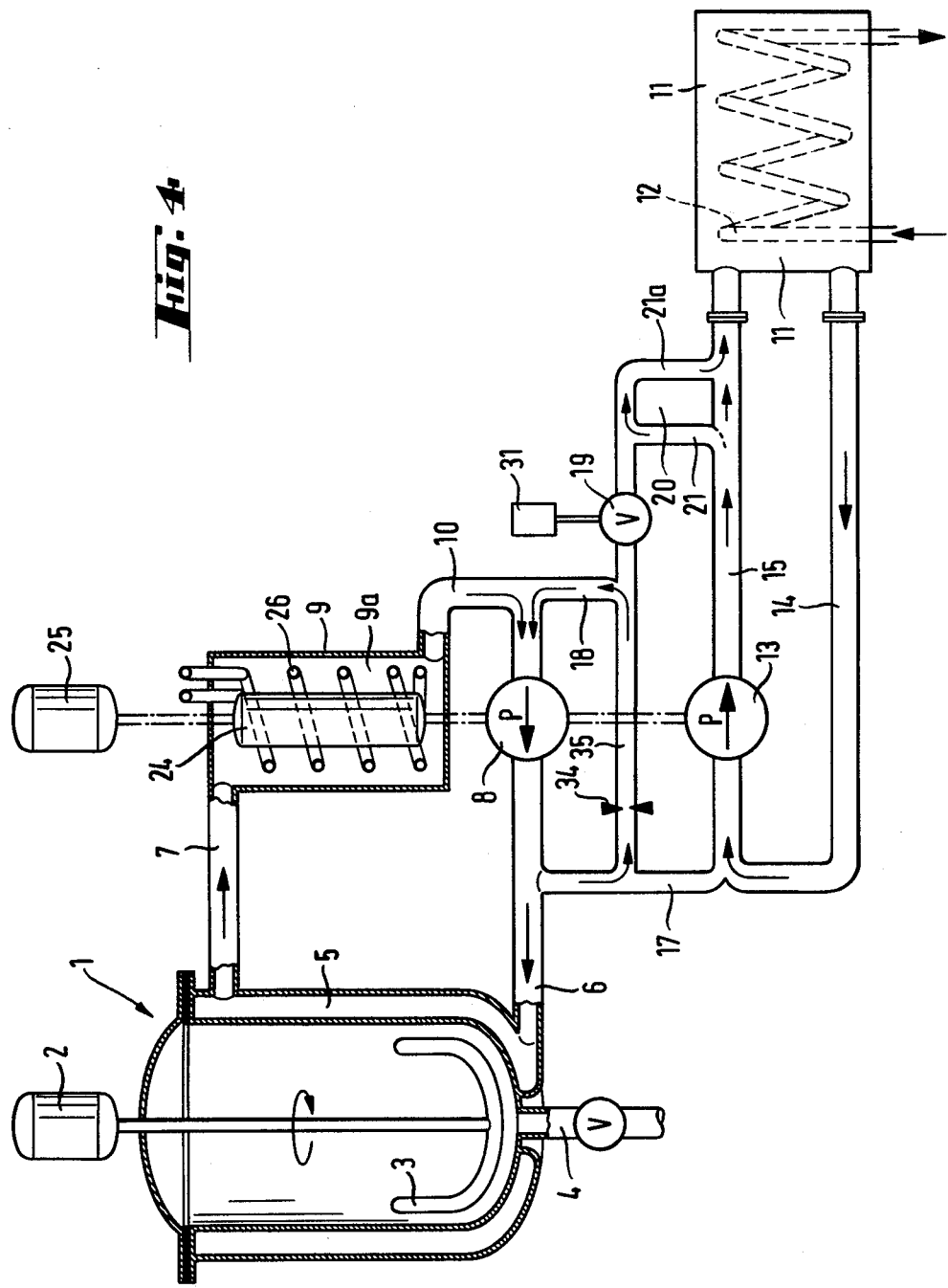
Figure 5:
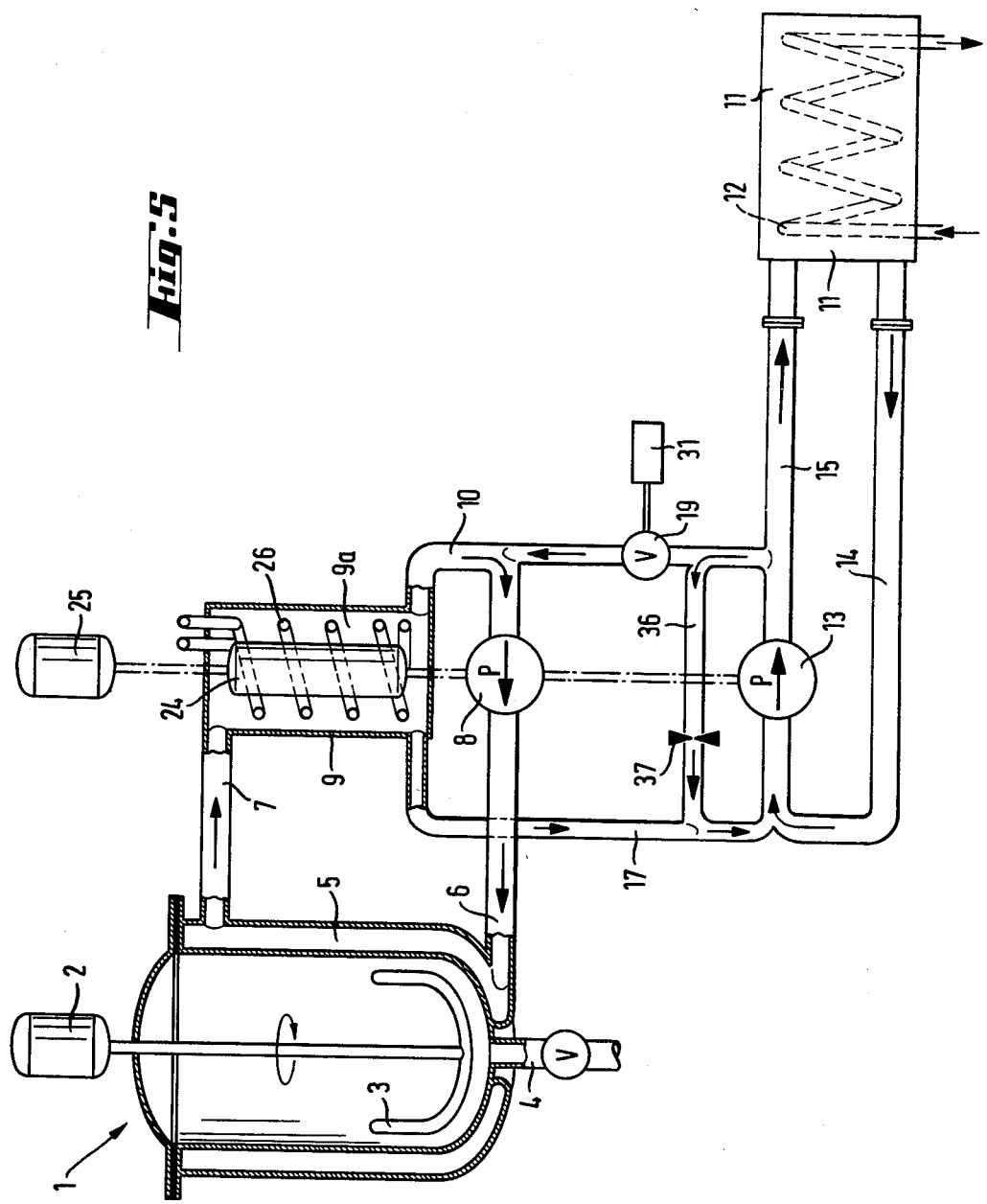
Figure 6:
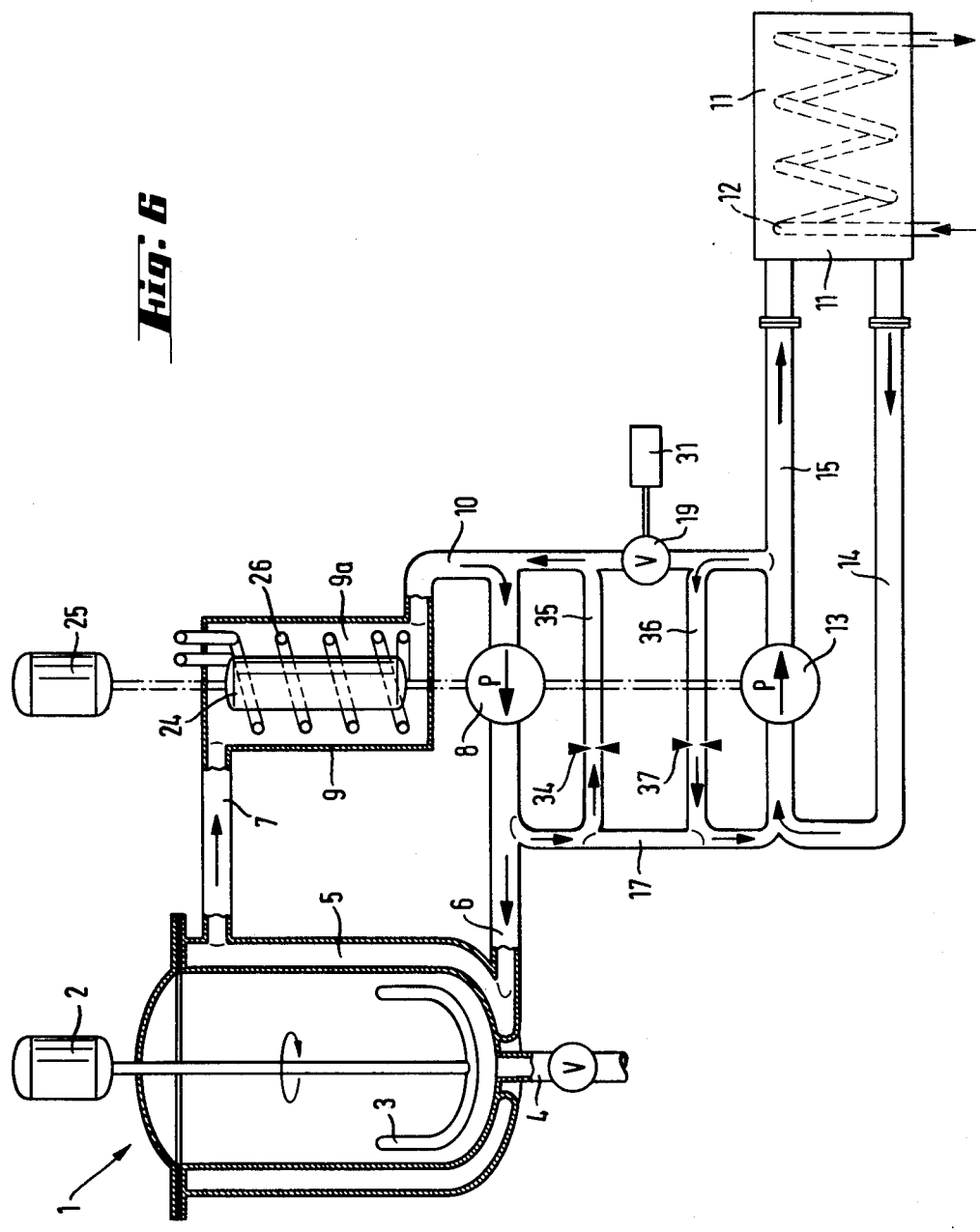

In FIGS. 4 to 6, three variants of the heat flow calorimeter according to FIG. 1 are schematically shown and like parts are designated by the same reference numerals.

These three variants only differ essentially from the one according to FIG. 1 in the connection of the cooling circulation system with the main circulation system.

In the variant according to FIG. 4 the return flow line 17 is not connected with the heating chamber 9 but rather with the duct 6 of the main circulation system. Furthermore, the circulating pump 8 is bypassed by a line 35 containing a shutter 34. In this flushing circulation system formed by this bypass line 35 and the circulating pump 8, a pickup stream circulates which takes care that at the outlet of valve 19 the heat transfer medium coming from the cooling circulation system is immediately transported away. In the loop 20 described hereinbefore, there flows a preparatory stream which constantly brings fresh medium to the inlet of valve 19.

In the case of the variant according to FIG. 5, the flashing loop 20 of FIG. 1 has been replaced by a bridging line 36 having a restrictor 37, which bridges the circulation pump 13 of the cooling circulation system. The preparatory stream circulates in this case through the cycle constituted by the bridging line 36 and the circulation pump 13. The remaining parts of this embodiment are the same as those of the variant according to FIG. 1.

In the variant according to FIG. 6, finally, the features of the two variants according to FIGS. 4 and 5 are combined in that the circulating pump 8 of the main circulation system as well as the circulating pump 13 of the cooling circulation system are each bypassed by a line 35 or 36, respectively, and the return flow line 17 is connected with the duct 6 of the main circulation system.

Figure 7:
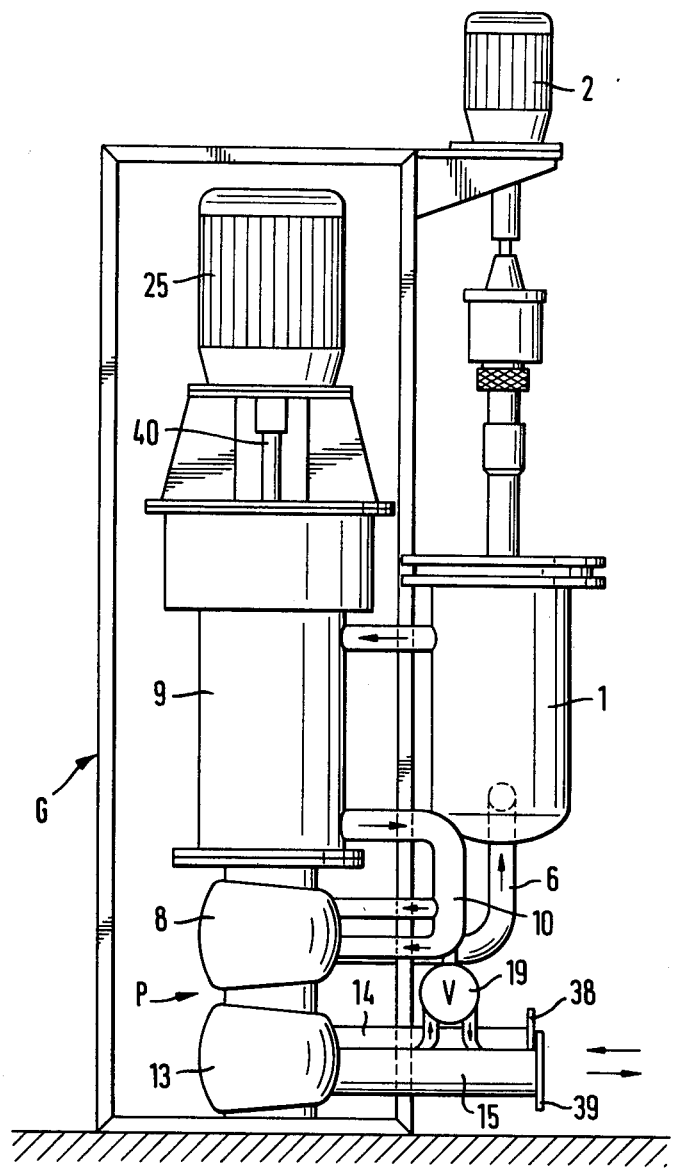

FIG. 7 illustrates how the heat flow calorimeter according to the invention can be constructed, for instance, as an apparatus. The calorimeter consists therein essentially of three structural units which are mounted in a frame G and connected by diverse lines according to the diagrams of one of FIGS. 1 or 4 to 6. These units are the reaction vessel 1 with the stirrer drive 2, the heating chamber 9, and a pump unit P containing the two circulating pumps 8 and 13, as well as the common driving motor 25 for the pumps and the displacement body 24 in the heating chamber 9. Pump unit P comprises a common pump housing for the two pumps 8 and 13 with a flange and two pump impellers mounted on a common shaft. The upper pump 8, in the drawing, of the main circulation system is a double-suction pump and has two connections for the inlet duct 10 which is split into two branches, as well as a connection for the drain duct 6. The lower pump 13 has one connection each, for the inlet duct 14 and for the drain duct 15 of the cooling circulation system. Flanges 38 and 39 serve for mounting the heat exchanger necessary for the cooling circulation system.

The heating chamber 9 is mounted on the flange of the pump housing. The pump shaft is directly coupled with the drive shaft of the displacement body 24 or its driving motor 25, respectively, so that the displacement body 24 and the two pump impellers are actually driven by a common shaft 40. In this manner an especially compact construction form is obtained.

The heat flow calorimeter according to the invention is superior to the known heat flow calorimeters of the same type in several respects. First of all, it is substantially more compact in its dimensions because it does not need separate reservoir tanks for hotter and colder heat transfer medium. Furthermore, the temperature regulation in the tanks for the now superfluous reserves of the two media which regulation is costly and necessarily is as precise as possible, is now no longer required, so that the entire regulation is considerably simpler and more reliable, also because of the smaller amount of measured values. Finally, only a single system is required, which responds relatively quickly to influence the temperature of the main circulation chamber, namely, by the admixture of cooler medium from the cooling circulation system, which latter is subject to no special requirements, as the circulation system temperature is controlled anyway.

What is claimed is:

1. A heat flow calorimeter comprising
(A) a reaction vessel;
(B) a heat exchange reactor mantle about said vessel;
(C) a main circulation system for circulating a heat transfer medium therethrough, said reactor mantle being part of said system;
(D) main circulating means for circulating said medium in said main circulation system and having a pressure side and suction side;
(E) a first source of cooled circulation medium linked to said main circulation system;
(F) heating means for heating said heat transfer medium in said main circulation system;
(G) temperature sensor means for detecting the temperatures prevailing in said reaction vessel, said reactor mantle and said first source;
(H) electronic regulator means responsive to said temperature sensors and adapted for controlling the temperature of said heat transfer medium as required by said sensors, through cooling the same, by supply of cooled circulation medium from said first source, or heating said heat transfer medium in said heating means;
in accordance with a desired temperature distribution in at least one of said reaction vessel and said reactor mantle;
said electronic regulator means comprising recording means for recording the time behavior of at least one of the following data:
(i) the temperature $(T_R)$ in the reactor and $(T_J)$ in the reactor mantle;
(ii) the temperature difference $(T_R - T_J)$;
said first source constituting a separate cooling circulation system which comprises
(a) a circulating pump having a pressure side and a suction side,
(b) a cold-generating source, and
(c) accessory duct means for completing said cooling circulation through (a) and (b); and
(I) valve means comprising a valve which links said first source to said main circulation system by connecting the pressure side of said circulating pump of said cooling circulation system with the suction side of said main circulating means with a minimum of dead volume, said valve having an entry side and an outlet side.

2. The heat flow calorimeter of claim 1, wherein said cooling circulation system additionally comprises a line connecting the suction side of said circulating pump with the main circulation system.

3. The heat flow calorimeter of claim 1 or 2, wherein said cold generating source comprises a heat exchanger and connecting lines for the passage of a cooling medium therethrough.

4. The heat flow calorimeter of claim 2, wherein said cooling circulation system comprises a bypass loop to which said valve is connected.

5. The heat flow calorimeter of claim 2 or 4, wherein the valve is directly connected with the inlet side of said circulating means of said main circulation system.

6. The heat flow calorimeter of claim 1 or 2, wherein said heating means comprise an electrical heating coil.

7. The heat flow calorimeter of claim 1, wherein said heating means comprise a subtantially cylindrical chamber having a cross-section substantially larger than said circulation ducts and being inserted in said main circulation system, a substantially cylindrical displacement body coaxially arranged in said chamber and an electrical heating coil arranged in the hollow space between said displacement body and the inner wall of said chamber.

8. The heat flow calorimeter of claim 7, wherein said heating means comprise a motor for rotating said displacement body.

9. The heat flow calorimeter of claim 1, wherein said main circulation system comprises a motor having a drive shaft adapted for driving said main circulating means and said circulating pump of said cooling circulation system in common by means of said drive shaft.

10. The heat flow calorimeter of claim 8 or 9, wherein said displacement body is driven by the same motor and over the same drive shaft as said main circulating means.

* * * * *